United States Patent [19]

Bae et al.

[11] Patent Number: 5,424,210
[45] Date of Patent: Jun. 13, 1995

[54] EXCLUSIVE KIMCHI FERMENTOR APPARATUS

[75] Inventors: Kil S. Bae, Gwachun; Jae I. Kim, Seoul; Mong S. Kang; Young M. Kim, both of Suweon, all of Rep. of Korea

[73] Assignee: Samsung Electronics Co., Ltd., Suwon, Rep. of Korea

[21] Appl. No.: 175,676

[22] Filed: Dec. 30, 1993

Related U.S. Application Data

[63] Continuation of Ser. No. 952,255, Sep. 28, 1992, abandoned.

[30] Foreign Application Priority Data

Sep. 26, 1991 [KR] Rep. of Korea ............... 91-16797

[51] Int. Cl.⁶ ............ C12M 1/36; A23B 4/12; A01J 11/00; A23C 3/02
[52] U.S. Cl. .................. 435/289; 435/290; 435/291; 435/813; 435/819; 426/7; 426/61; 99/468; 99/470; 99/483; 99/486
[58] Field of Search ............ 435/289, 290, 291, 316, 435/813, 819; 426/7, 8, 49, 52, 61, 270, 404, 506, 636, 617; 99/468, 470, 483, 486; 165/2, 30, 58; 62/152, 155; 422/109

[56] References Cited

U.S. PATENT DOCUMENTS

| 3,633,374 | 1/1972 | Canter | 62/202 |
| 3,968,660 | 7/1976 | Amann et al. | 62/275 |
| 4,086,780 | 5/1978 | Dienemann | 62/174 |
| 4,332,142 | 6/1982 | Prada | 62/152 |
| 4,701,415 | 10/1987 | Dutton et al. | 435/289 |
| 5,142,969 | 9/1992 | Chun | 99/468 |
| 5,220,807 | 6/1993 | Bourne et al. | 62/238.6 |
| 5,228,499 | 7/1993 | Yoon | 165/2 |

FOREIGN PATENT DOCUMENTS 3812440 10/1989 Germany ............... 435/289

Primary Examiner—Robert J. Warden
Assistant Examiner—Christopher Y. Kim
Attorney, Agent, or Firm—Burns, Doane, Swecker & Mathis

[57] ABSTRACT

An exclusive kimchi fermentor includes at least two chambers for selectively fermenting and storing kimchi. The apparatus preferably includes a fan and a heater for curing kimchi in a least one chamber during a fermentation mode. The apparatus also preferably includes an evaporator for supplying cool air into at least one of the chambers during a storage mode. A microprocessor controls the heater and the evaporator in order to selectively place the chambers in the fermenting mode or the storage mode.

2 Claims, 12 Drawing Sheets

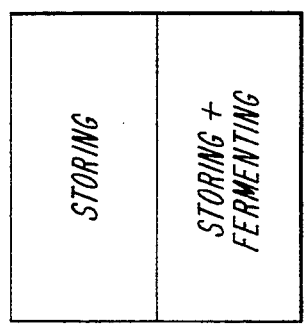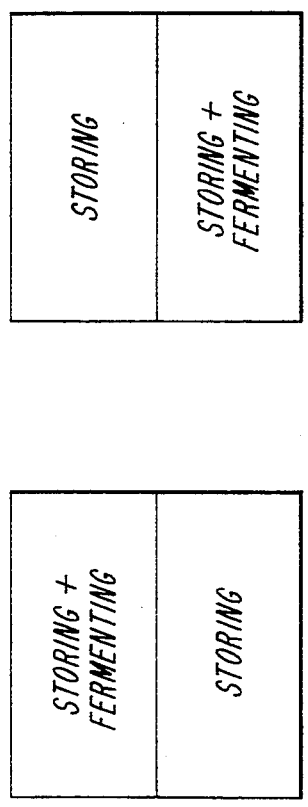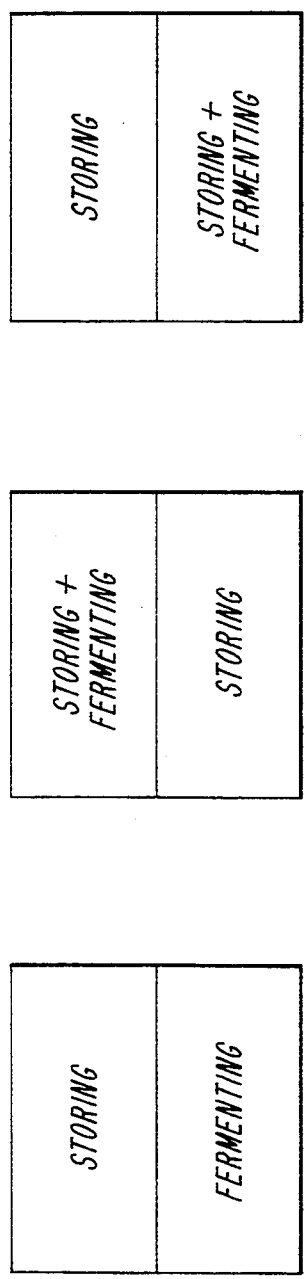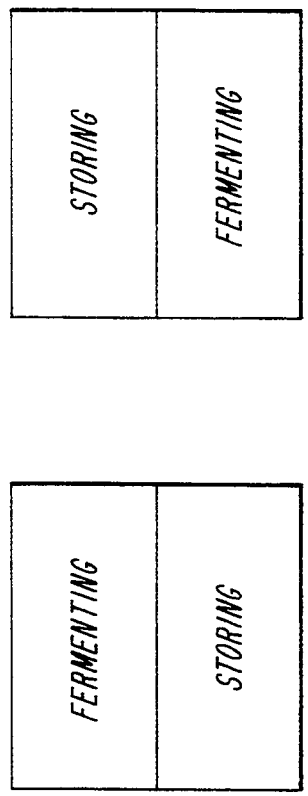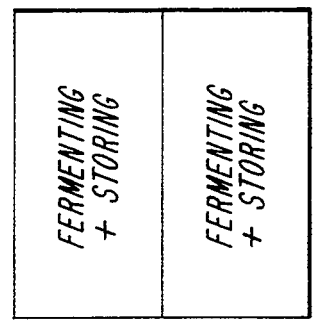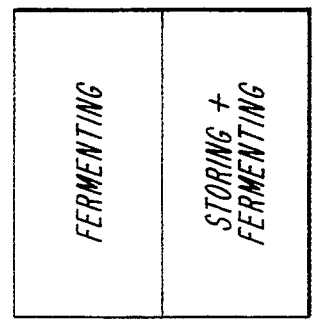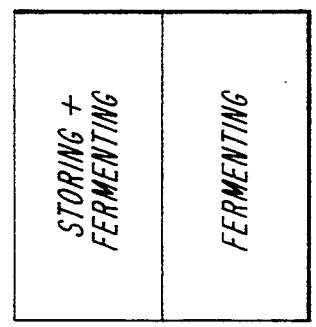

EXCLUSIVE KIMCHI FERMENTOR APPARATUS

This application is a continuation of application Ser. No. 07/952,255, filed Sep. 28, 1992, now abandoned.

BACKGROUND OF THE INVENTION

The invention relates to a pickling vegetable fermenting and/or storing apparatus, and more particularly, to an exclusive pickled vegetable fermentor apparatus comprising at least two chambers for fermenting vegetables and/or storing the fermented or pickled vegetables (especially kimchi which is a particular pickled cabbage).

BACKGROUND OF THE DISCLOSURE

Generally, pickled vegetables, especially kimchi, are a naturally fermented food based on unique freshness, sourness together with the tastes of various condiments. Kimchi tastes are chiefly dependent upon the degree of fermentation, in which the optimum degree of fermentation is normally the maximum time that the fermentation mechanism is operative.

Fermentation relies mainly on temperature and time. Raising the temperature means a faster fermentation rate. The temperature is raised by heating the fermentation vessel. Thus, temperature and time are fairly crucial to fermentation. Once fermented, kimchi easily acidifies or sours at room temperature. This causes difficulties in marketing properly cured kimchi and preserving it for a long period. Thus, the inherent taste of kimchi cannot be easily maintained, because stored kimchi continues to ferment, thereby losing its unique taste.

Typically, refrigerators are used to preserve kimchi along with other general foodstuffs for relatively long periods of time. But, the conventional refrigerator is limited in the storage of kimchi since fermentation is not stopped. Storing kimchi in a refrigerator ignores the curing degree of the stored kimchi. Kimchi stored in the refrigerator is not considered to be adequately stored, since fermentation occurs even at the temperature of the conventional refrigerator after being completely cured. It is known that kimchi produces a unique odor, which greatly influences the taste of other foodstuffs stored with it. Also, kimchi changes its curing state when in storage, thereby causing undesirable tastes. Therefore, kimchi stored for a long period in a refrigerator does not have the right taste.

There has been provided a fermentor for controlling the fermentation time and temperature in order to ferment kimchi to a desirable cured state as well as to maintain the resulting product at a proper storage temperature. The fermentor was divided into a freezing chamber and a refrigerating chamber, like a present-day refrigerator, in which the refrigerating chamber is for kimchi fermentation and storage. Alternatively, a portion of the freezing and refrigerating chambers may be partitioned to form an additional kimchi fermentation or storage chamber. The fermenting kimchi storage chamber includes a heating member mounted therein for maintaining the chamber at the optimum fermentation temperature for kimchi for a predetermined curing period, in which the kimchi is completely fermented through the initial curing step. Thereafter, the kimchi is stored at the predetermined temperature under a storage mode activated by a sensor for detecting the desired state of completion of the kimchi fermentation.

Another conventional kimchi fermenting/storing chamber, however, is based on switching between the fermentation mode and the storage mode in an ongoing operation, i.e., using the same chamber. However, it is impossible to use the fermentation and storage functions at the same time. In other words, the stored or fermented kimchi must be moved to another storage chamber in order that new kimchi may be prepared, i.e., to initiate fermentation in the chamber. In this case, the completely cured kimchi must be moved to a refrigerating chamber and may be stored at a temperature, which is not proper considering the uniqueness of kimchi, thereby losing the inherent taste of the fermented product.

Accordingly, it is desirable to provide an exclusive kimchi fermentor for solving the problems such that kimchi may be prepared to have the right taste as well as stored for a long period while maintaining its taste. It is most preferable to develop an exclusive kimchi fermentor for preparing kimchi considering the types of vegetables, the bacteria, the physiological phenomena of the salt concentration, and temperature, all of which play an important role in cultivating the bacteria for proper fermentation.

It is the main object of the present invention to provide an exclusive kimchi fermentor for fermenting and/or storage.

It is another object of the present invention to provide an exclusive kimchi fermentor for fermenting and/or storing using a conventional freezing cycle to balance the other conditions except for the natural fermentation and the temperature conditions relative to kimchi materials including radishes, cabbages and cucumbers.

It is still another object of the present invention to provide an exclusive kimchi fermentor provided with at least two chambers, each of which is able to be operated in the fermentation mode or the storage mode.

It is still another object of the present invention to provide an exclusive kimchi fermentor provided with at least two chambers, in which one chamber has the fermentation and storage functions, and the other chamber provides the storage function, and vice versa.

It is still another object of the present invention to provide an exclusive kimchi fermentor provided with at least two chambers, in which one chamber has the fermentation and storage functions, and the other chamber performs the fermentation function, and vice versa.

It is still another object of the present invention to provide an exclusive kimchi fermentor provided with at least two chambers, each of which has the fermentation and storage functions which may be independently utilized separate from the other chamber.

In order to achieve these objects and features, the present invention is intended to maintain at least two chambers at the kimchi fermenting and/or storing temperature using the freezing cycle of a conventional refrigerator or a heating member. Also, the present invention may be adapted to a refrigerator of a direct or indirect cooling type.

SUMMARY OF THE INVENTION

According to the present invention, an exclusive kimchi fermentor comprises at least two chambers, each of which is selectively provided with a means for fermenting kimchi through heating and a means for circulating heated air inside the chamber to perform the fermentation and a means for freezing and for storing the completed kimchi.

In other words, each chamber has a fermentation function and a storage function. Each chamber can be switched between the fermentation and storage functions. Each chamber is provided with a heater and a cooling means. The cooling means is adapted to a freezing cycle, and it includes a compressor, a means for cooling the inner portion of the chamber and a means for selectively controlling the operation of the cooling means. Therefore, each chamber includes the fermentation function and the storage function which operate separately and independently from each other.

Another embodiment of the present invention is an exclusive kimchi fermentor which comprises at least two chambers with each chamber having the fermentation and storage functions which are switchable from each other.

BRIEF DESCRIPTION OF THE DRAWINGS

For a fuller understanding of the nature and objects of the invention, references should be had to the following detailed description taken in conjunction with the accompanying drawings in which.

DETAILED DESCRIPTION OF THE INVENTION

The preferred embodiment of the present invention will be now described in detail with reference to the accompanying drawings.

Figure 1:
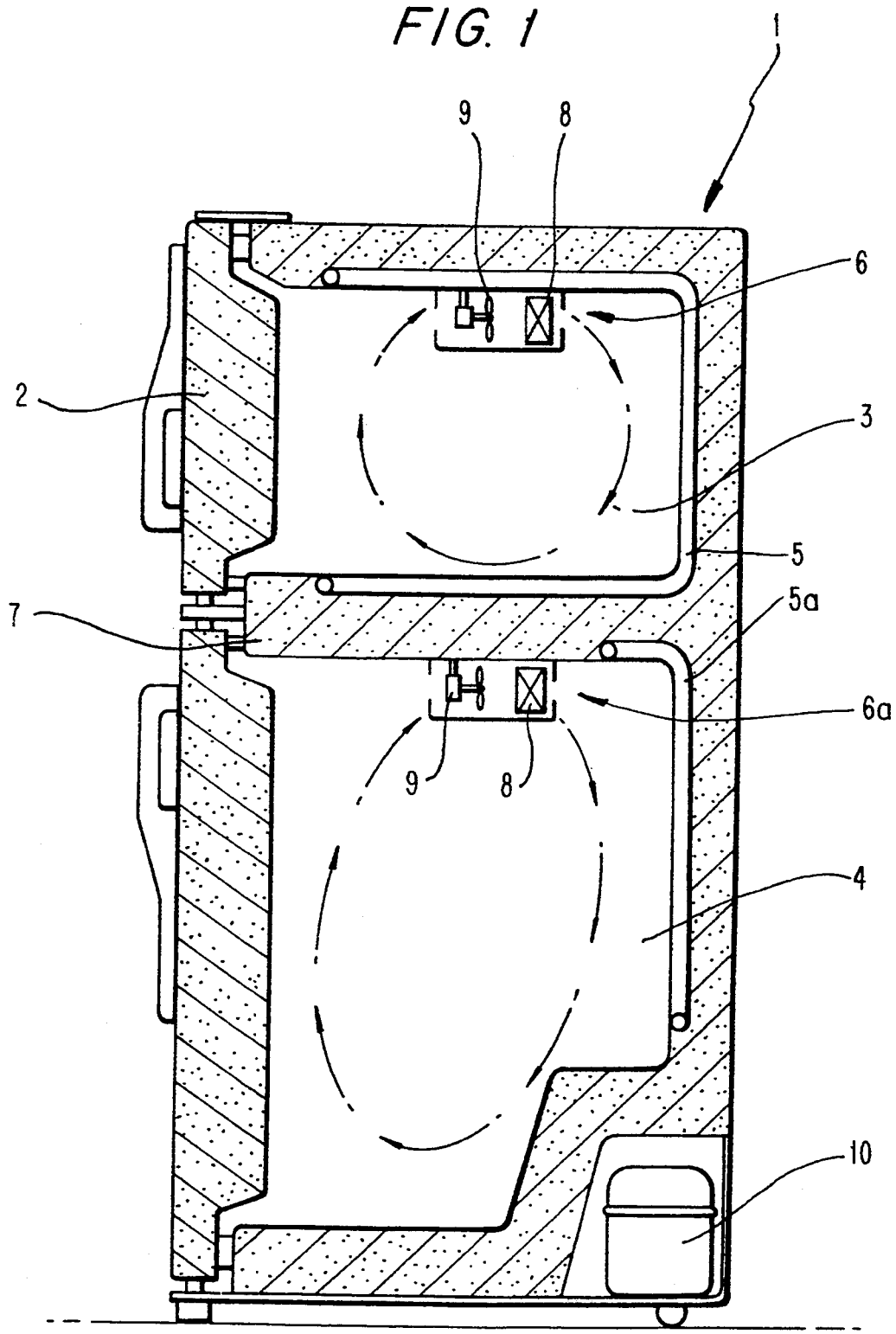
FIG. 1 is a schematic view of the typical configuration illustrating an exclusive kimchi fermentor according to the preferred embodiment of the invention.

FIG. 1 is a schematic view showing one embodiment of an exclusive kimchi fermentor of a direct cooling type which is adapted to the present invention. The exclusive kimchi fermentor is provided with a body 1. Means embodying the present invention are illustrated in the drawings and installed in the body for the convenience of the description.

The body 1 is provided with an upper chamber 3 and a lower chamber 4, each with a corresponding door 2 capable of being separately opened/closed. The upper and lower chambers 3 and 4 have cooling air passageways in order to adjust their inner temperatures for storage of cured kimchi which is associated with the freezing cycle. Herein, the freezing cycle is the same as that of a conventional refrigerator. A compressor, an evaporator, a condenser, a capillary tube and related refrigeration apparatuses are used, and they are under control of a microprocessor according to a set program which is hereinafter described in detail. The temperature of the storage chamber according to the present invention is adjusted to a predetermined temperature suitable for the physiological condition of kimchi. Also, chambers 3 and 4 may be divided into a multitude of parts if necessary. These chambers may be provided with coolers 5, 5a adjacent and surrounding the inside wall thereof in order to maintain the inner temperature at a kimchi storage temperature. There is an evaporator coil, and a compressor 10 mounted at the lower portion of the body 1 as described in drawings. Fermenting devices 6 and 6a are respectively mounted in the inner upper portion of each of chambers 3 and 4 in order to establish the proper conditions for fermenting kimchi by raising the temperature within chamber.

Additionally, the fermentation devices 6 and 6a are mounted in the top portion of each of the upper and the lower chambers 3 and 4. The fermentation devices 6 and 6a include a heater member 8 for raising the chamber temperature and a ventilating device 9 for circulating the heated air in the chamber. These devices are referred to as a load.

The upper and lower chambers 3 and 4 are separately divided into the upper and lower portions of the body 1 by a partition wall 7 with a cooler 5 positioned in each inner wall thereof similar to a conventional refrigerator of the direct cooling type.

Figure 2:
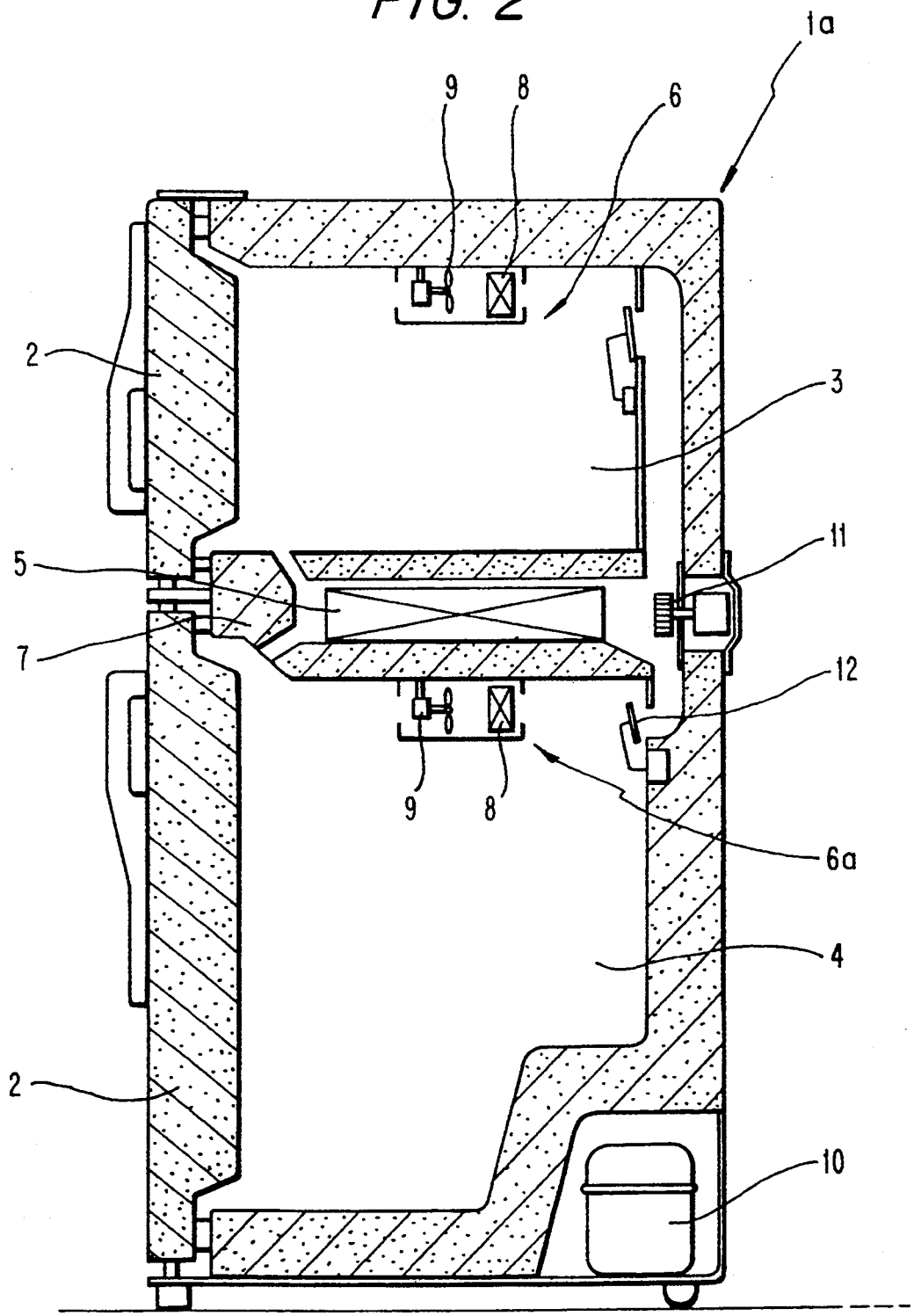
FIG. 2 is a schematic view of the typical configuration illustrating an exclusive kimchi fermentor according to another preferred embodiment of the invention.

A further embodiment is illustrated in FIG. 2. In this embodiment the body 1a of the fermentor is of an indirect type.

The difference from the fermentor of FIG. 1 is that the fan 11 for forcing cool air during a cooling cycle is provided near to the cooler 5 for supplying cool air into the upper chamber 3 and the lower chamber 4. Cooler 5 is an evaporator. A damping device 12 for changing the chamber temperature into the storage mode is positioned in each chamber.

Figure 3:
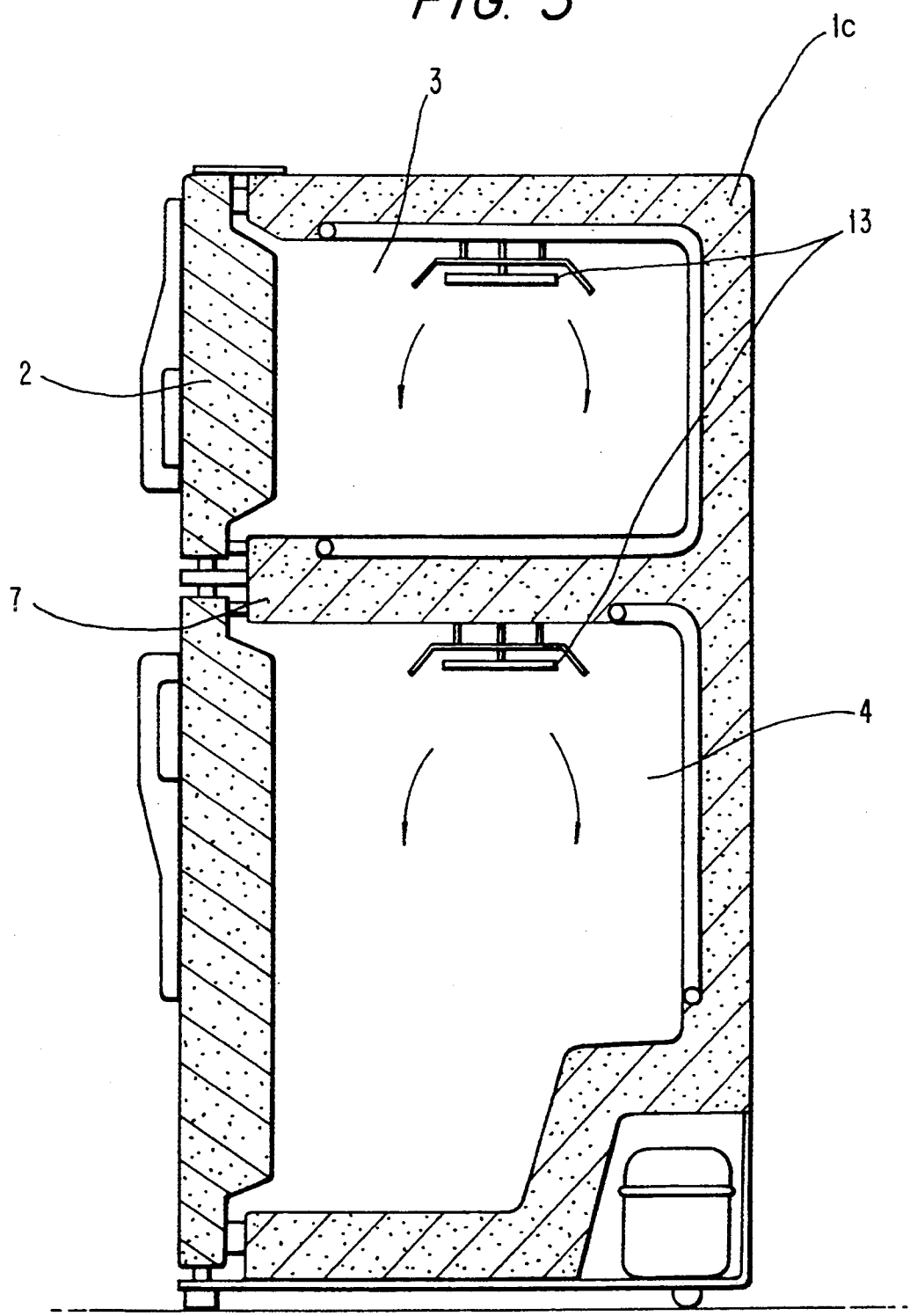
FIG. 3 is a schematic view of the typical configuration illustrating an exclusive kimchi fermentor according to another preferred embodiment of the invention.

FIG. 3 is an example which is different from either FIG. 1 or FIG. 2. The fermentation device of the invention can bring on fermentation by natural convection. Accordingly, an exclusive kimchi fermentor adapted to a refrigerator of a direct or an indirect type comprises a body 1c like the embodiment shown in FIG. 3. Body 1c also produces the same cooling cycle as the first embodiment and also it is divided into chambers 3, 4 by the partition wall 7.

The fermentation devices 6, 6a in the first embodiment each comprises a ventilating fan 9 and a heating member 8. In FIG. 3, chambers 3 and 4 are provided with a heater 13 at each respective upper wall thereof. The heater 13 is a heating member for changing the interior temperature into one suitable to promote fermentation.

Figure 4:
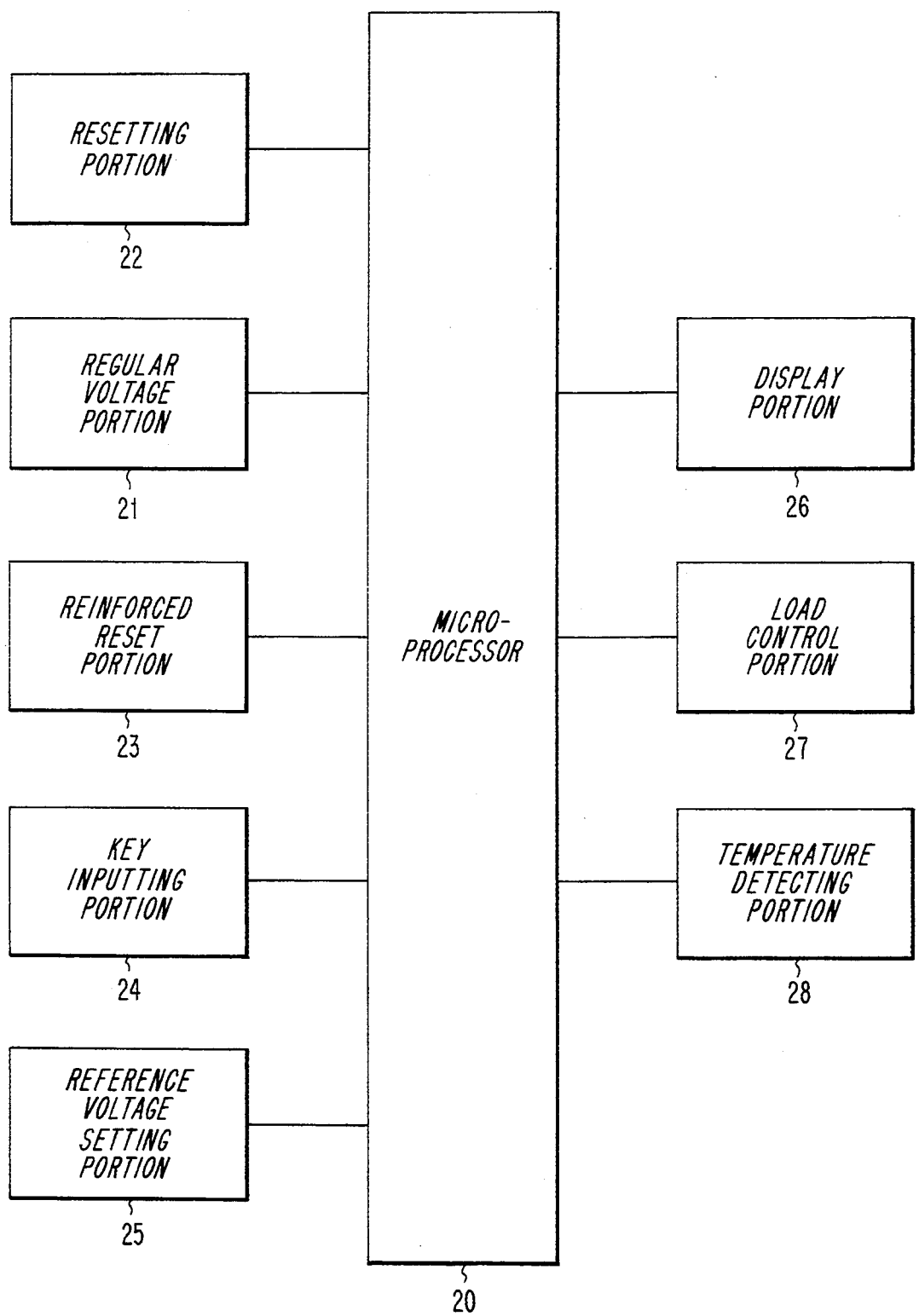
FIG. 4 is a view illustrating the configuration of a micro-processor and its peripheral parts used in an exclusive kimchi fermentor.

The present invention further comprises a microprocessor 20 for controlling the loads of a compressor, a heater and a fan according to the program memorized in advance as illustrated in FIG. 4.

This microprocessor 20 as shown in FIG. 4 is provided with a reset portion 22 for performing initialization. A load portion 27 controls each of the loads such as the cooler 5, the fan 11, the damping device 12, the heating member 8 and so on. A display portion 26 shows the operational state of each load. A temperature detecting portion 28 detects the inner temperature of each chamber 3, 4.

The microprocessor 20 is also coupled to a key inputting portion 24 for ordering the operation of each load. The upper and the lower chambers 3, 4 are ordered to ferment or cure and store kimchi. A regular voltage portion 21 supplies an operating voltage to each circuit. A second reset portion 23 resets the microprocessor 20 for safety when heating or when there is an error in operation. The reference voltage setting portion 25 supplies an analogue/digital converting standard voltage to the microprocessor 20 when necessary.

Figure 5A:
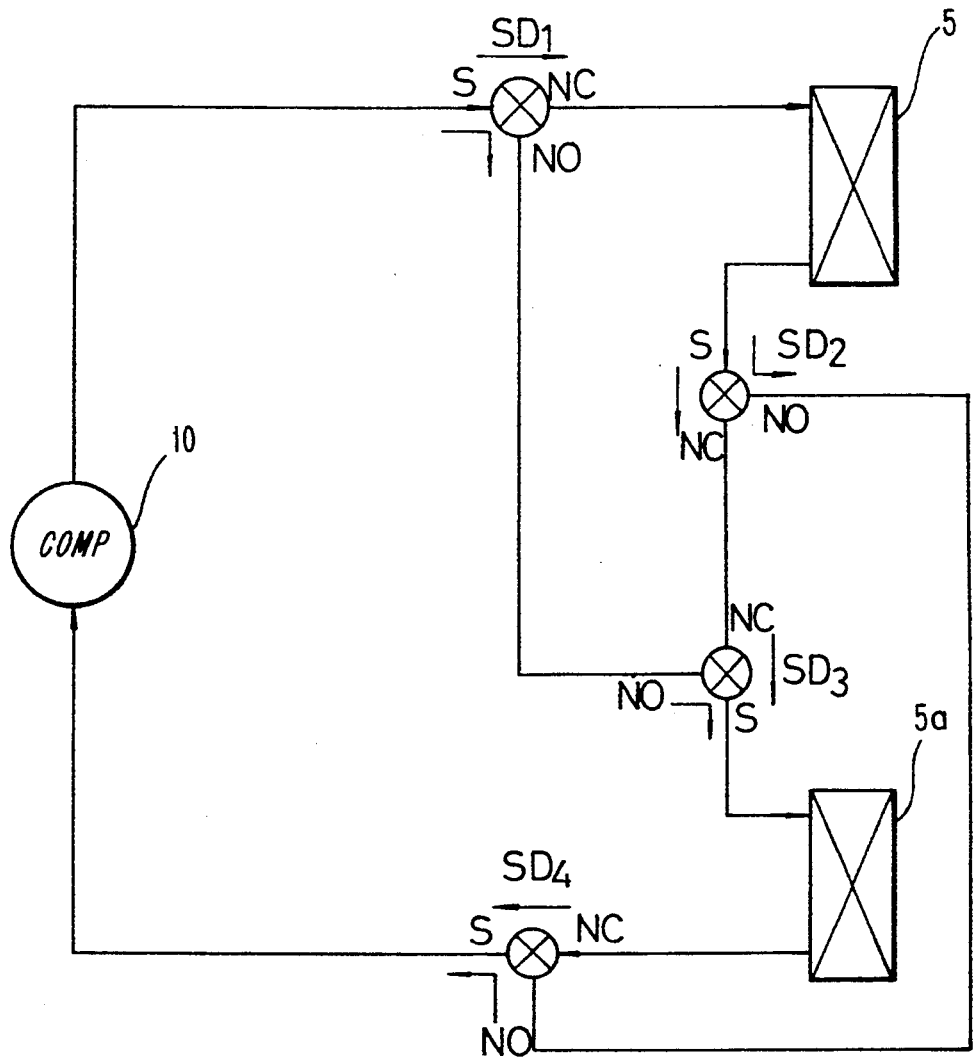
FIG. 5A is a view showing a cooling cycle.

On the other hand, FIG. 5A which is related to FIG. 1, shows one example of the operation of the exclusive kimchi fermentor comprising two coolers utilizing the freezing cycle according to the invention.

Referring to FIG. 5A, the compressor 10 is connected with the cooler 5 by a T type solenoid valve SD1 and also the cooler 5a by a T type solenoid SD4. The coolers 5 and 5a each supply cool air into the upper chamber 3 and lower chamber 4.

Figure 5B:
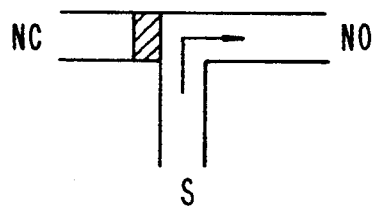
FIGS. 5B and 5C are views illustrating the operation of a solenoid of a T type depending on an electric power source.
Figure 5C:
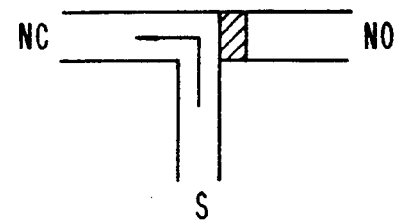

In addition, the upper chamber cooler 5 can be connected with the lower chamber cooler 5a by T type solenoid valves SD2 and SD3 or with the compressor by T type solenoid valves SD2 and SD4. The lower chamber cooler 5a can be directly connected to the compressor 10 by T type solenoid valves SD1 and SD3. FIG. 5B shows the Normal Closed position NC and the Normal Open position NO which are dependent upon the application of power from the power source. For example, the application of power to the T type solenoid valve FIG. 5B causes the closed terminal, called Normal Closed, to provide a refrigerant flowing passage. A discussion concerning the condenser used in the cooling cycle is eliminated for the sake of brevity, since it is appreciated by those skilled in the art.

Therefore, in connection with the upper chamber 3 and the lower chamber 4, the cooling cycle for the upper and the lower chambers occurs when the refrigerant passageway is established from the compressor 10, through solenoid valve SD1 to the upper chamber cooler 5, through solenoid valves SD2 and SD3 to the lower chamber cooler 5a and back to compressor 10. If the solenoid valve SD1 is turned on to supply the upper chamber cooler 5 and if solenoid valves SD2 and SD4 are turned off isolating lower cooler 5A, the refrigerant passageway is established from the compressor 10, through solenoid valve SD1 through the upper chamber cooler 5, through solenoid valve SD2, through solenoid valve SD4 and back to the compressor 10 for supplying cool air to the upper chamber 3. This refrigerant passageway represents "the upper chamber cooling execution".

For providing cool air to only the lower chamber 4, solenoid valves SD1, SD2 are off, thereby isolating upper chamber 3. The solenoid valve SD3 is on to form the refrigerant passageway from the compressor 10, through the solenoid valve SD1, through the solenoid valve SD3 and through the lower chamber cooler 5a, through the solenoid valve SD4 and back to the compressor 10. This refrigerant passageway represents "the lower chamber cooling execution".

When one intends to ferment kimchi in the upper and the lower chambers 3, 4, the operation of the heating members 8 stops the operation of the compressor 10. Simultaneously, the ventilating devices 9 selectively circulates the heat generated by the heating members 8 in each chamber 3, 4 (FIGS. 1 and 2) or the heaters 13 generate heat by natural convection (FIG. 3).

Accordingly, while the raw kimchi in each chamber 3 or 4 in the body of the fermentor ferments, the temperature sensor 29 monitors the fermentation temperature.

When the kimchi stored in the chamber 3, 4 reaches an ideally fermented state, a sensor detects this state and provides a signal to the microprocessor 20, thereby stopping the operation of the fermentation devices 6, 6a. Simultaneously, the operation of compressor 10 is initiated.

The coolers, therefore, keep the temperature in each chamber at the optimum storage maintaining temperature in order to store the ideally fermented kimchi for a long time in a fresh state.

The microprocessor 20 can perform a storing/storing mode, a storing/fermenting mode, a fermenting/storing mode and a fermenting/fermenting mode in connection with each chamber 3, 4.

Figure 6:
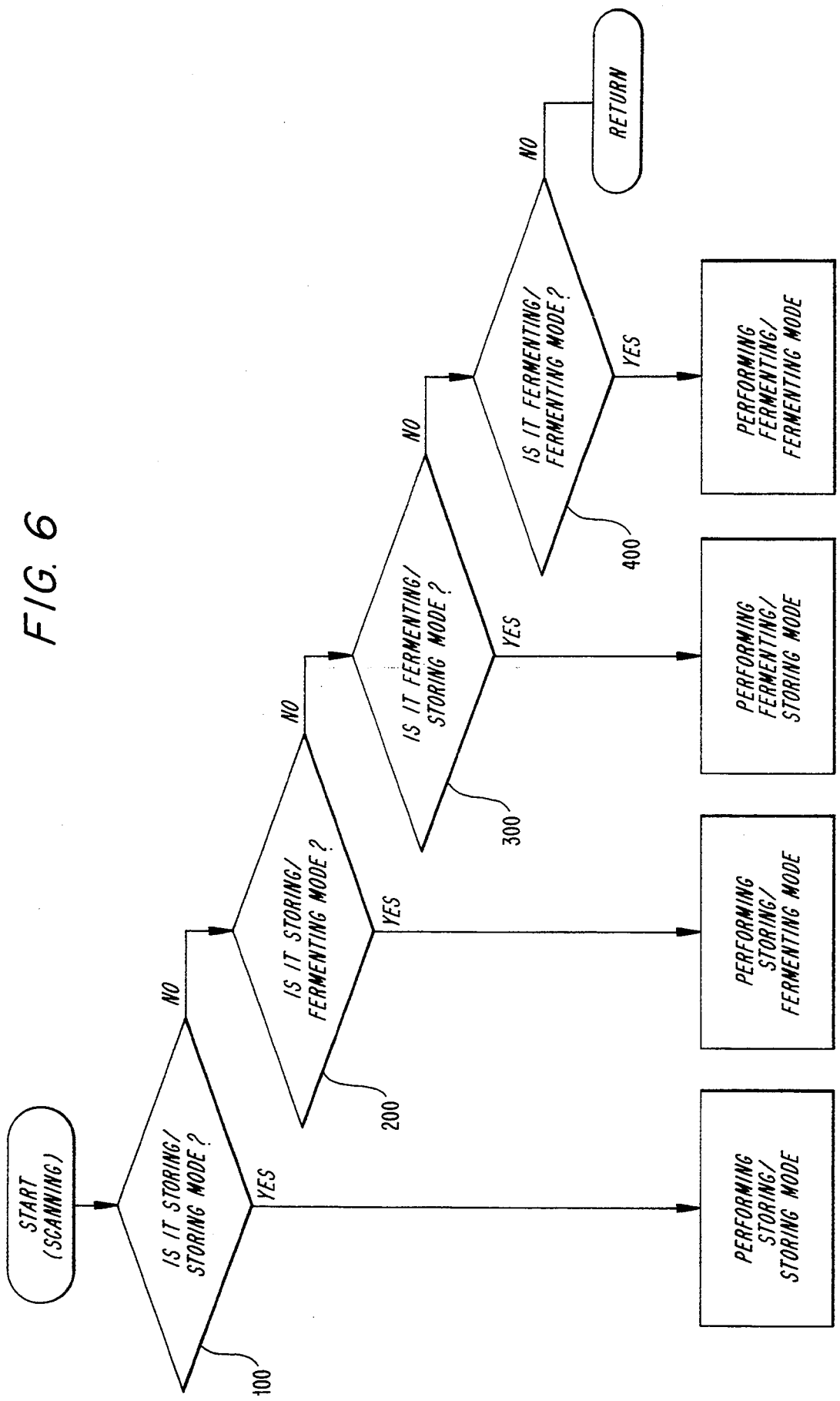
FIG. 6 is a flow chart illustrating the operation of each chamber of an exclusive kimchi fermentor including the selection of a desirable function mode to be performed according to the invention.

The microprocessor 20 initially sets the chambers 3 and 4 to the desired mode by scanning the input signals from the key inputting portion 24 in order to verify the current function mode as shown in FIG. 6.

In other words, the microprocessor 20 ascertains the desired mode by judging whether the present mode is the storing/storing mode, the storing/fermenting mode, the fermenting/storing mode or the fermenting/fermenting mode through the steps 100, 200, 300 and 400.

Figure 7:
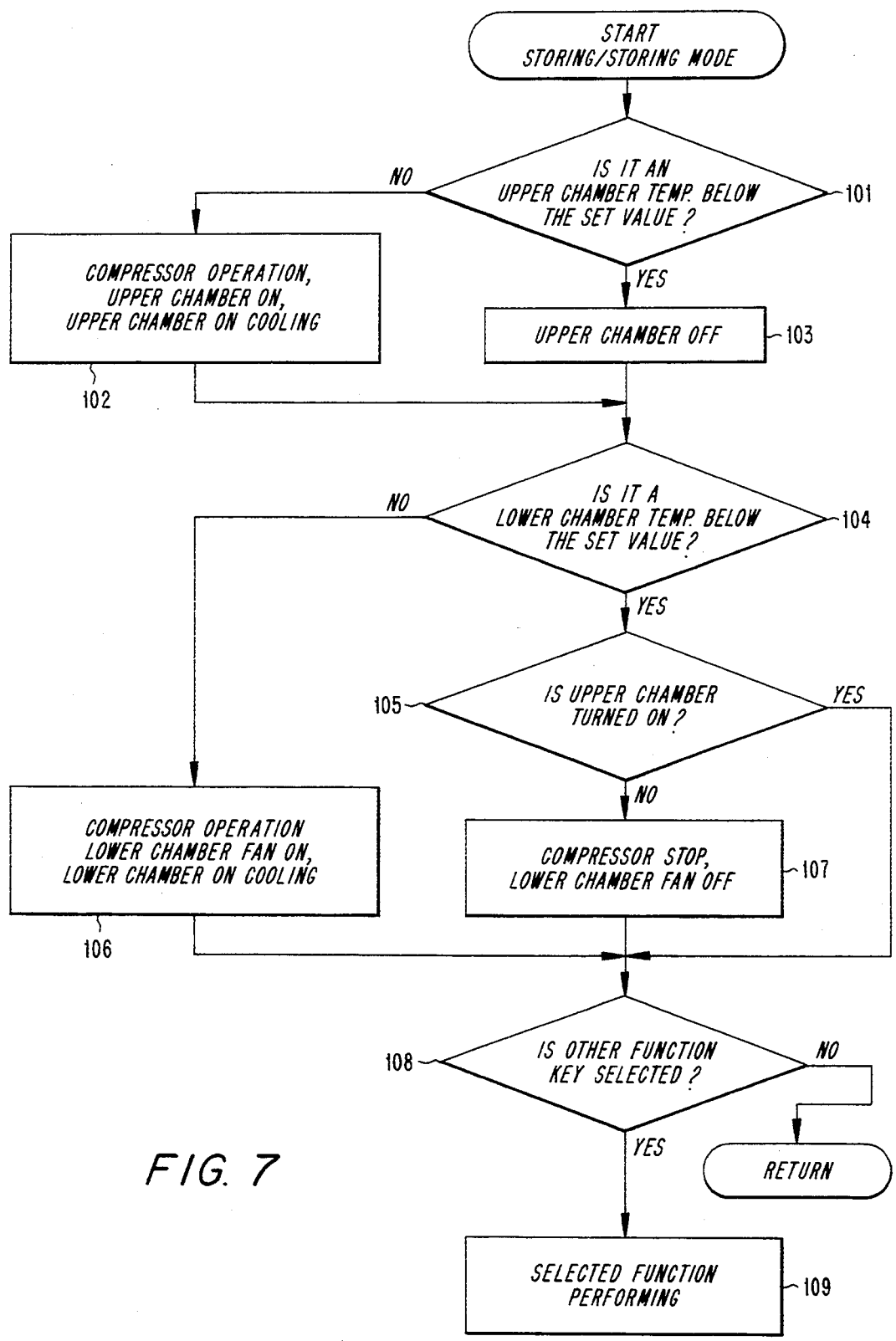
FIG. 7 is a flow chart illustrating the storing/storing mode which is performed in each chamber of an exclusive kimchi fermentor according to the invention.

Accordingly, to execute the storing/storing mode (FIG. 7), the microprocessor judges whether the upper chamber 3 temperature is below a predetermined value at step 101. If the temperature is below, it turns off the upper chamber fan 9 (used for cooling) at step 103. If the temperature is above, it operates the compressor 10 at step 102 and turns on the upper chamber fan 9 to cool the upper chamber. At the next step 104, the microprocessor judges whether the lower chamber temperature is below the predetermined value. If it is above, it turns on the lower chamber fan 9 at step 106 and operates the compressor 10 to initiate the lower chamber cooling. If it is below, it judges whether the upper chamber fan 9 is turned on or not at step 105. If the fan 9 is on, it advances to step 108, and in the reverse case (fan off), it stops compressor 10 and turns off the lower chamber fan at step 107. At step 108, it judges whether another key is selected or not. If a function key is selected, the control advances to step 109 in order to perform the designated function, or if not, it returns to continue the control.

Figure 8:
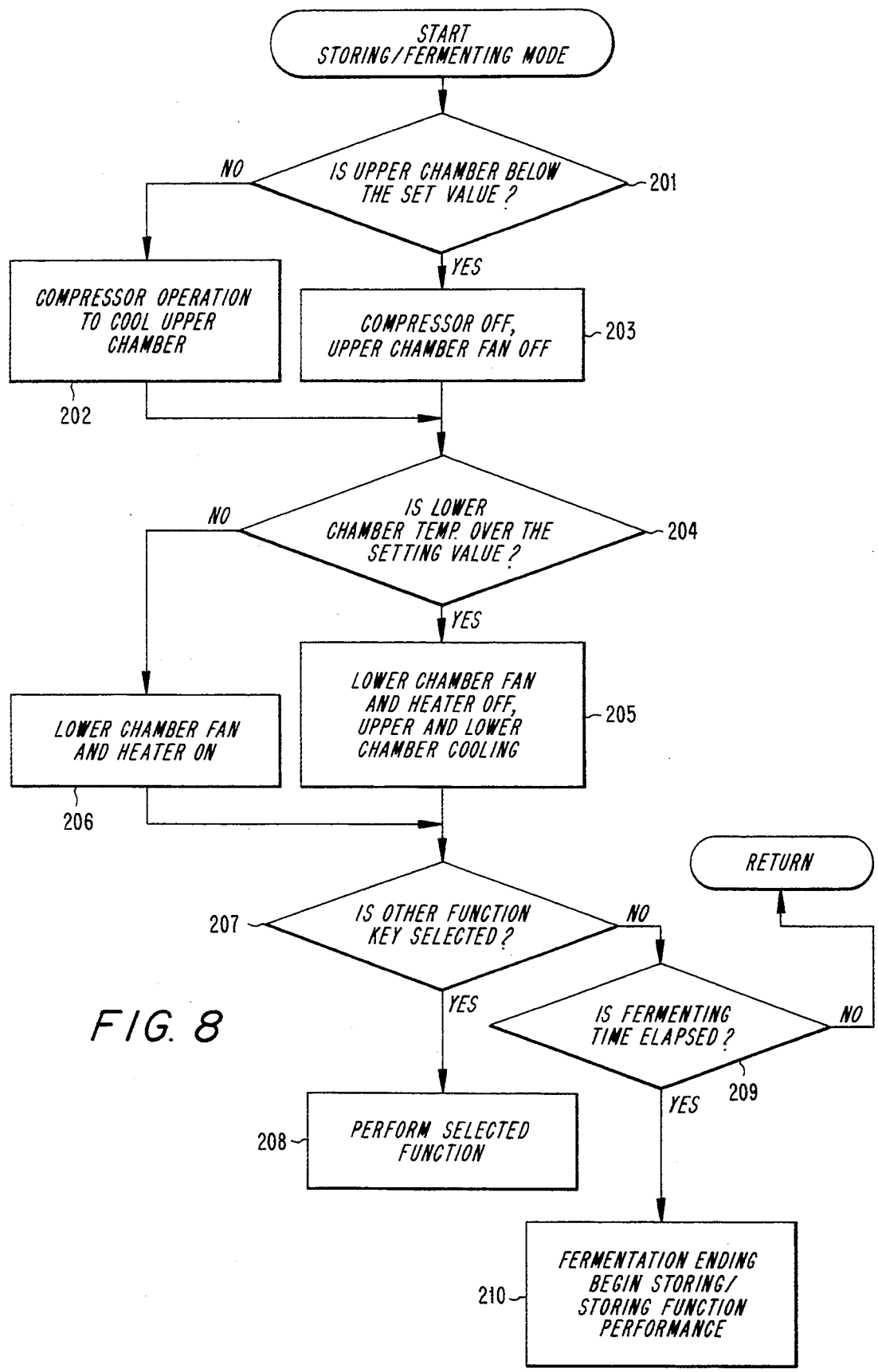
FIG. 8 is a flow chart illustrating the storing/fermenting mode which is performed in each chamber of an exclusive kimchi fermentor according to the invention.

The following steps execute the storing/fermenting function as shown in FIG. 8.

At step 201, the microprocessor judges whether the upper chamber temperature is below a predetermined value. If it is above, it operates the compressor 10 at step 202 and turns on the upper fan 9 to initiate the upper chamber cooling. If the temperature is below, at step 203, it stops the compressor 10 and turns off the upper chamber fan 9. The microprocessor then judges whether the lower chamber temperature is above the predetermined value at step 204. If the temperature is above, the control flows to step 205 to turn off the lower chamber fan 9 and the heater, thereby initiating cooling of the upper and the lower chambers. In the reverse case (temperature below), it turns on the lower fan 9 and the heater at step 206. At the next step 207, the microprocessor judges whether the other function key is chosen. If another function key is designated, it performs the chosen function at step 208 and if not, it progresses to step 209. At step 209, it judges whether the fermentation time has lapsed. If the time has elapsed, it ceases the fermentation at step 210 and converts the function to the storing/storing mode.

Figure 9:
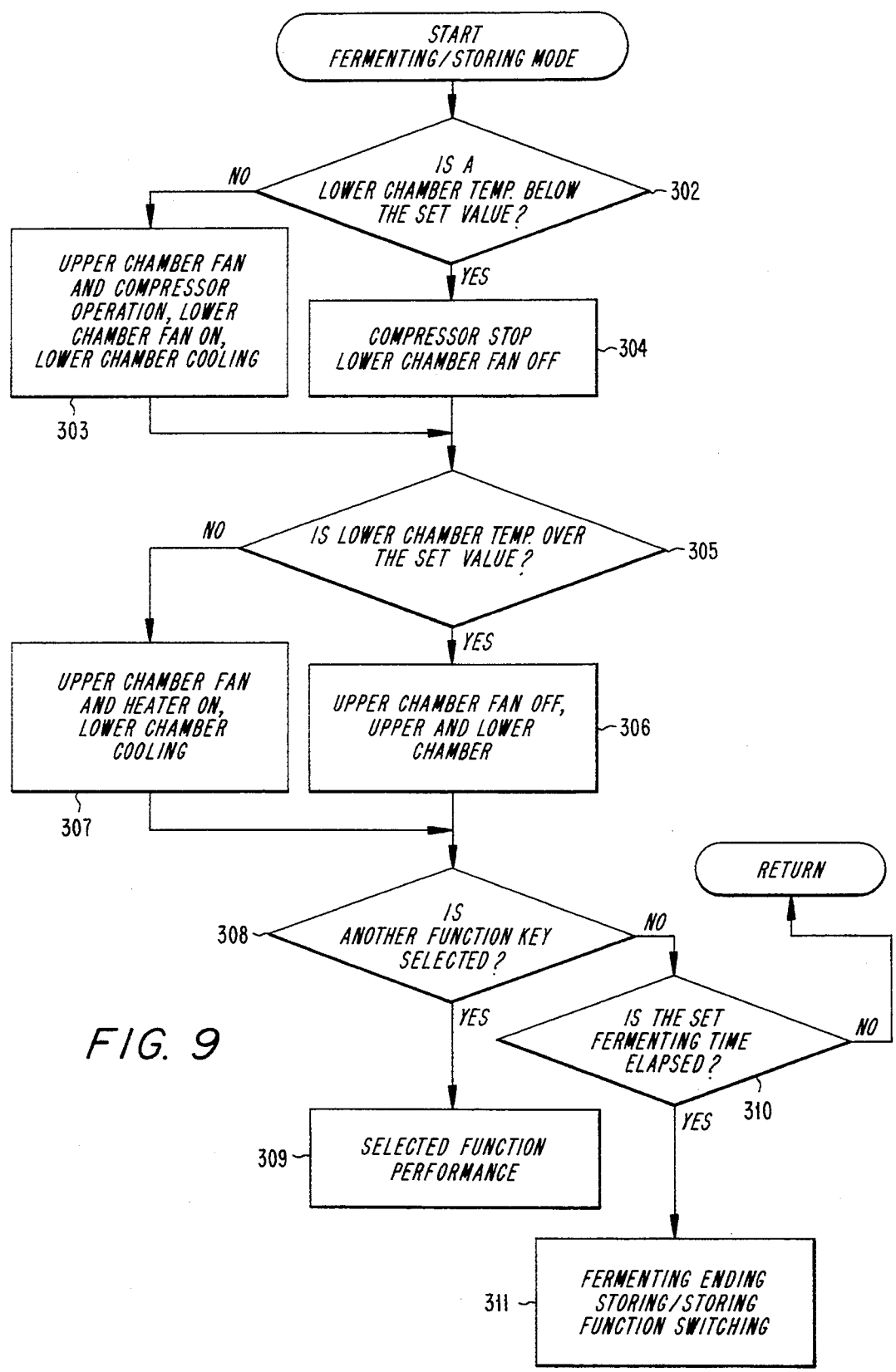
FIG. 9 is a flow chart illustrating the fermenting/storing mode which is performed in each chamber of an exclusive kimchi fermentor according to the invention.

FIG. 9 shows the execution of the fermentation and storage functions in the upper and lower chambers, respectively.

At step 302, the microprocessor judges whether the lower chamber temperature is below the predetermined value. If it is below, it ceases the operation of the compressor 10 at step 304 and turns off the lower chamber fan 9. If it is above, it advances toward step 303 to operate the compressor 10, the upper chamber fan and heater, and the lower chamber fan, in order to attain lower chamber cooling and upper chamber fermentation.

At step 305, it judges whether the upper chamber temperature is above the predetermined value. If it is above, it turns off the upper chamber fan and the heater at step 306, and it causes upper and lower chamber cooling. If it is below, it turns on the upper chamber fan and the heater at step 307, and it causes lower chamber cooling.

At the next step 308, it judges whether another function key is selected. If selected, it executes the selected function at step 309. If not, it progresses to step 310 to judge whether the predetermined fermentation time has elapsed. After the fermentation time has elapsed, it ceases the fermentation at step 311 and changes the function to the storing/storing mode.

Figure 10A:
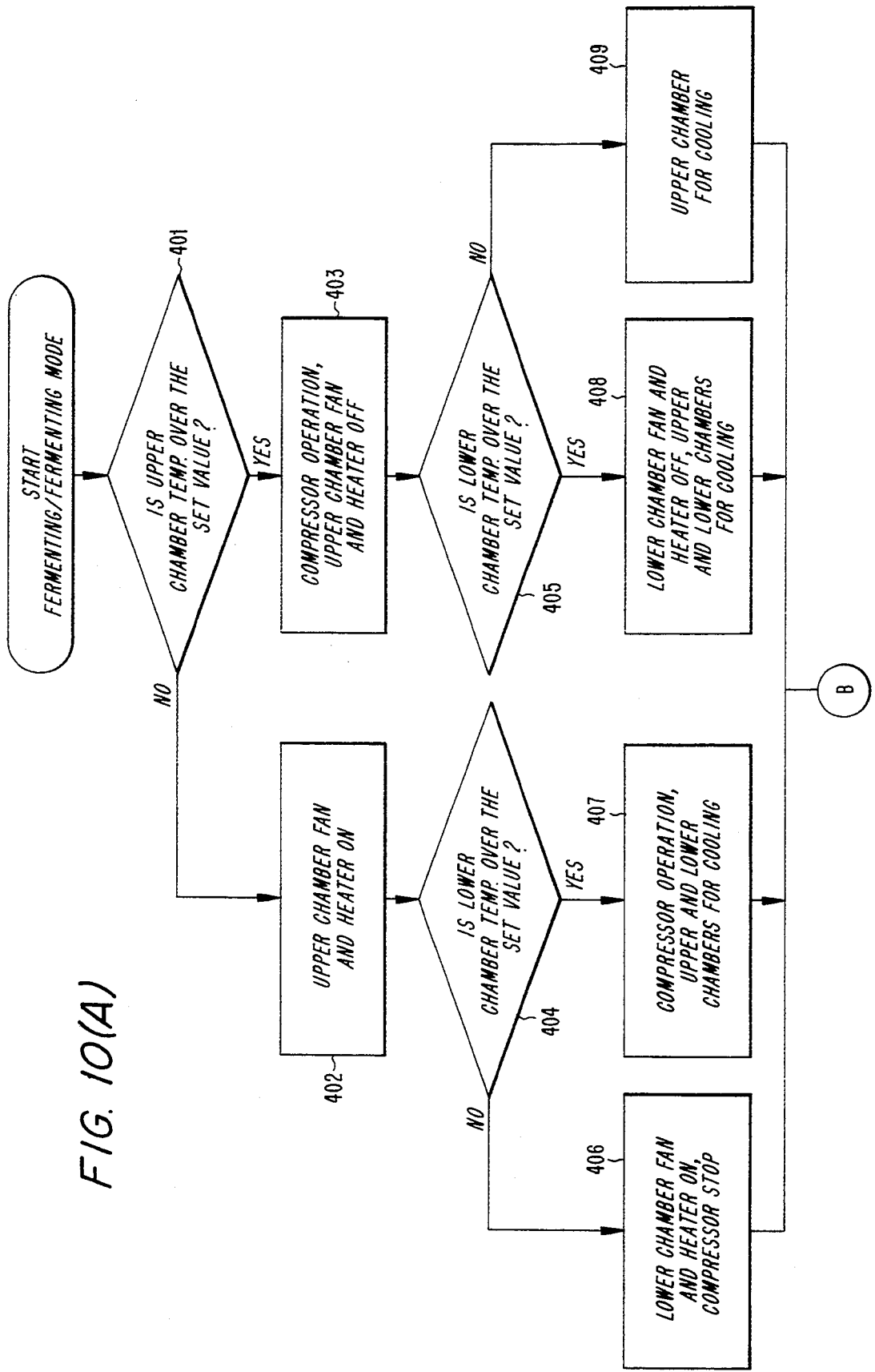
FIGS. 10A and 10B are a flow chart illustrating the fermenting/fermenting mode which is performed in each chamber of an exclusive kimchi fermentor according to the invention; and, FIG. 11 is a plurality of illustrative examples showing the possibility of a configuration that may be constructed as an exclusive kimchi fermentor according the principle of the invention.
Figure 10B:
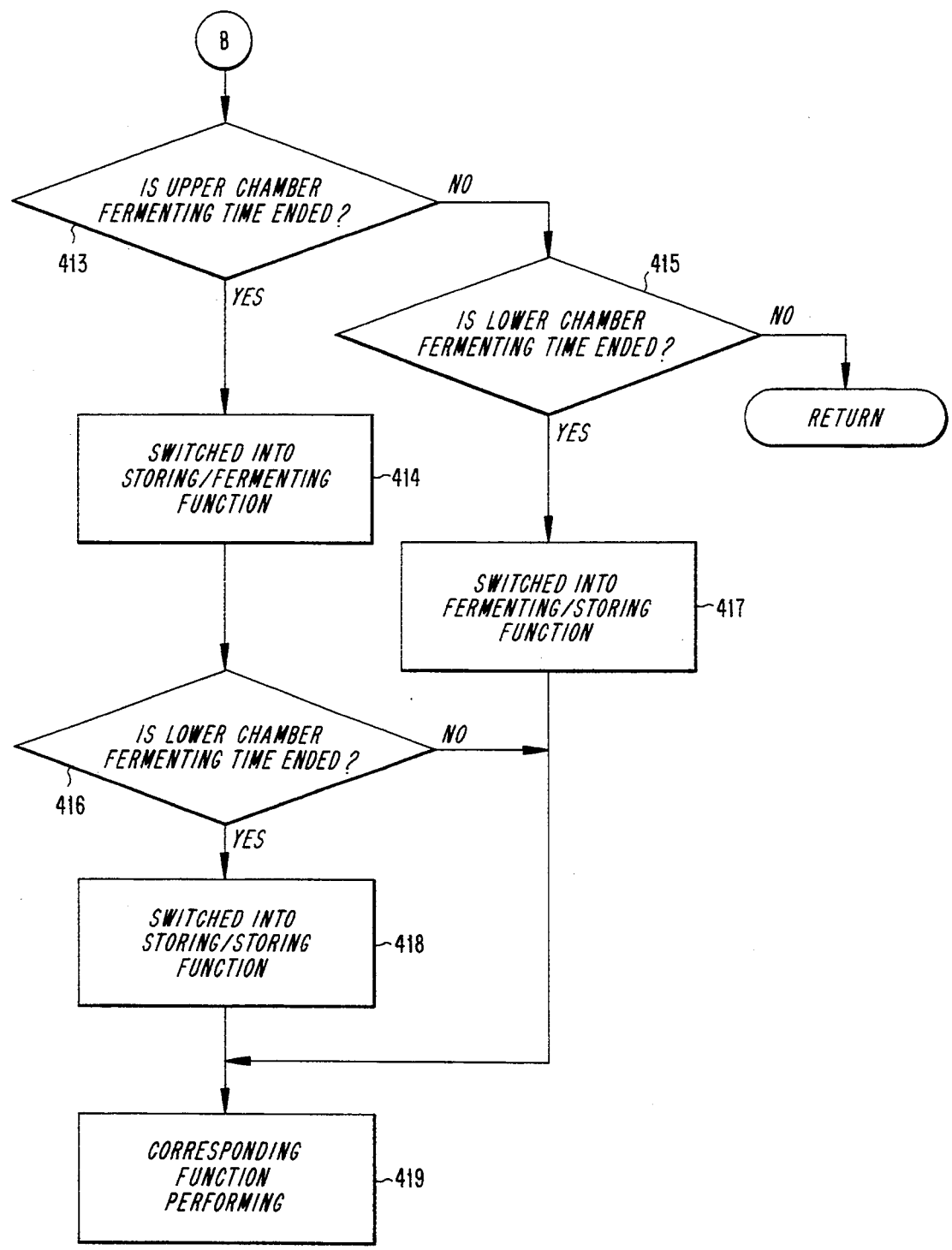

FIGS. 10A and 10B represents the execution of the fermenting/fermenting function for the upper and lower chambers, respectively.

If a user selects the fermenting/fermenting function key, the microprocessor judges whether the temperature is above the predetermined value. When the temperature is not over the set value, it turns on the upper chamber fan and the heater at step 402.

At step 404, it judges whether the temperature is above the predetermined value in the lower chamber. If it is, it operates the compressor 10 at step 407 to initiate lower chamber cooling for only the lower chamber, in order to control the temperature. If the lower chamber temperature is below the set value, it turns on the lower chamber fan and heater and stops the operation of the compressor 10 at step 406.

If the upper chamber temperature is above the predetermined value at the step 401, it turns off the upper chamber fan and heater at step 403 and operates the compressor 10 in order to cool the upper chamber. At step 405, it judges whether the lower chamber temperature is above the predetermined value. If it is above, at step 408, it turns off the lower chamber fan and heater and cools the upper and the lower chambers.

At step 405, if the lower chamber temperature is below the predetermined value, it executes the upper chamber cooling for supplying cool air only to the upper chamber in order to control the temperature.

At the next step 413, it judges whether the fermentation time of the upper chamber has elapsed during the predetermined term. If the time has elapsed, it converts the function to the storing/fermenting mode. The microprocessor also judges whether the fermentation time of the lower chamber has exceeded the predetermined time at step 416. If it has been exceeded, it changes the function to the storing/storing mode at step 418.

At step 413, if the time for fermentation has not been exceeded, it judges whether the fermentation time of the lower chamber fermentation has elapsed or not at step 415. If the time has elapsed, the function is converted to the fermenting/storing mode.

Accordingly, the invention is operated as described above and as shown in FIG. 11.

In FIG. 11A the fermenting function and storing function are performed by the upper chamber 3 and the lower chamber 4. The upper chamber 3 includes the fermentation devices 6 and 13 for performing the fermentation promoting function. The lower chamber 4 is used to only perform a storage function. A reversed functional arrangement is shown in FIG. 11B.

As shown in FIG. 11C, the upper chamber 3 is provided with fermentation devices 6 and 13 and cooling devices in order to be switchable between the fermentation and storage mode arrangement, thereby providing the storing/fermenting function. The lower chamber 4 can provide only the storage function or cooling function. It is also possible that the upper chamber 3 can be provided with only the storage function, while the lower chamber 4 has the storing/fermenting function as shown in FIG. 11D.

As shown in FIG. 11E, the upper chamber 3 is provided with the fermentation devices 6 and 13 and cooling devices in order to be switchable between the fermentation and storage mode arrangement to provide either the storage or the fermentation function. The lower chamber 4 includes only the fermentation devices to perform only the fermentation function. It is also possible that the upper chamber 3 can be provided with only the fermentation devices 6 and 13 to provide the fermentation function as shown in FIG. 11F, while the lower chamber 4 can be provided with the fermentation devices 6 and 13 and cooling devices to provide, storage and fermentation functions.

As shown in FIG. 11G, the upper chamber 3 includes the fermentation devices 6 and 13, and cooling devices in order to have storage and fermentation modes switchable from each other. The lower chamber 4 can be constructed to have the storage and the fermentation functions in the same way as the upper chamber as shown in FIG. 1 and FIG. 3.

Therefore, the invention can be selectively constructed to have the fermentation or the storage function, whereby it can perform mutually different functions as well as performing simultaneously the same functions.

Consequently, it is an advantage not only continue to produce kimchi but also to provide many kinds of kimchi.

We claim:
1. A kimchi fermentor comprising;
a housing including at least two chambers;
fermenting means for fermenting kimchi and placing each of said chambers in a fermenting mode, said fermenting means including means for indepen- dently circulating air which warms said two chambers to a predetermined heating temperature;

cooling means for supplying air to said two chambers which cools said two chambers to a predetermined storage temperature and for placing each of said chambers in a storage mode, said cooling means including a plurality of electronically controlled valves that regulate a supply of refrigerant in said cooling means and at least a compressor, a first cooling coil, and a second cooling coil, so that the electronically controlled valves regulate the flow of refrigerant through the first and second cooling coils and the compressor; and control means for controlling the fermenting means and the cooling means in order to place selectively each of said chambers in at least one of the fermenting mode and the storage mode, the control means including temperature sensing means and input means for controlling the supply of air to said chambers which warms said chambers to said predetermined heating temperature and for controlling the supply of air to said chambers which cools said chambers to said predetermined cooling temperature by actuating said electronically controlled valves.

2. An apparatus according to claim 1 wherein the control means further comprise means for controlling the valves allow the refrigerant to flow only through the first cooling coil in a first state, to flow only through the second cooling coil in a second state, and to flow through both the first and second cooling coils in a third state.

* * * * *